United States Patent [19]

Cordi et al.

[11] Patent Number: 4,997,821
[45] Date of Patent: Mar. 5, 1991

[54] PHOSPHONO-HYDROISOQUINOLINE COMPOUNDS USEFUL IN REDUCING NEUROTOXIC INJURY

[76] Inventors: Alexis A. Cordi, 13393 Amiot Dr., St. Louis, Mo. 63146; Michael L. Vazquez, 564 Running Creek, Ballwin, Mo. 63021

[21] Appl. No.: 260,839

[22] Filed: Oct. 21, 1988

[51] Int. Cl.$^5$ .................. C07F 9/60; A61K 31/675
[52] U.S. Cl. ........................ 514/82; 546/23
[58] Field of Search ................... 546/23; 514/82

[56] References Cited

U.S. PATENT DOCUMENTS 4,746,653 5/1988 Hutchison et al. .................. 514/89

OTHER PUBLICATIONS

March, Advanced Organic Chemistry, Reactions, Mechanisms and Structure, Second Edition, p. 462 McGraw Hill Pub. (1979).

*Primary Examiner*—Alan L. Rotman
*Attorney, Agent, or Firm*—J. Timothy Keane; Paul D. Matukaitis

[57] ABSTRACT

A class of phosphono-hydroisoquinoline componds is described for treatment to reduce neurotoxic injury associated with anoxia or ischemia which typically follows stroke, cardiac arrest or perinatal asphyxia. The treatment includes administration of a phosphono-hydroisoquinoline compound alone or in a composition in an amount effective as an antagonist to inhibit excitotoxic actions at major neuronal excitatory amino acid receptor sites. Compounds of most interest are those of the formula:

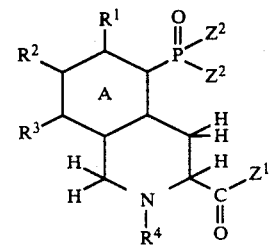

wherein each of $R^1$ through $R^4$ is hydrido, each of $Z^1$ and $Z^2$ is hydroxyl and wherein the A ring is aromatic.

27 Claims, No Drawings

PHOSPHONO-HYDROISOQUINOLINE COMPOUNDS USEFUL IN REDUCING NEUROTOXIC INJURY

FIELD OF THE INVENTION

This invention is in the field of clinical neurology and relates specifically to a class of compounds, compositions and methods for neuro-protective purposes such as controlling chronic or acute neurotoxic injury or brain damage resulting from neuro-degenerative diseases. For example, these compounds are particularly useful for treating neurotoxic injury which follows periods of anoxia or ischemia associated with stroke, cardiac arrest or perinatal asphyxia. The compounds would also be useful as anti-convulsants and analgesics.

BACKGROUND OF THE INVENTION

Unlike other tissues which can survive extended periods of hypoxia, brain tissue is particularly sensitive to deprivation of oxygen or energy. Permanent damage to neurons can occur during brief periods of hypoxia, anoxia or ischemia. Neurotoxic injury is known to be caused or accelerated by certain excitatory amino acids (EAA) found naturally in the central nervous system (CNS). Glutamate (Glu) is an endogenous amino acid which has been characterized as a fast excitatory transmitter in the mammalian brain. Glutamate is also known as a powerful neurotoxin capable of killing CNS neurons under certain pathological conditions which accompany stroke and cardiac arrest. Normal glutamate concentrations are maintained within brain tissue by energy-consuming transport systems. Under low energy conditions which occur during conditions of hypoglycemia, hypoxia or ischemia, cells can release glutamate. Under such low energy conditions the cell is not able to take glutamate back into the cell. Initial glutamate release stimulates further release of glutamate which results in an extracellular glutamate accumulation and a cascade of neurotoxic injury.

It has been shown that the sensitivity of central neurons to hypoxia and ischemia can be reduced by either blockage of synaptic transmission or by specific antagonism of postsynaptic glutamate receptors [see S. M. Rothman and J. W. Olney, "Glutamate and the Pathophysiology of Hypoxia—Ischemic Brain Damage", *Annals of Neurology*, Vol. 19, No. 2 (1986)]. Glutamate is characterized as a broad spectrum agonist having activity at three neuronal excitatory amino acid receptor sites. These receptor sites are named after the amino acids which selectively excite them, namely: Kainate (KA), N-methyl-D-aspartate (NMDA or NMA) and quisqualate (QUIS). Glutamate is believed to be a mixed agonist capable of binding to and exciting all three receptor types.

Neurons which have EAA receptors on their dendritic or somal surfaces undergo acute excitotoxic degeneration when these receptors are excessively activated by glutamate. Thus, agents which selectively block or antagonize the action of glutamate at the EAA synaptic receptors of central neurons can prevent neurotoxic injury associated with anoxia, hypoxia or ischemia caused by stroke, cardiac arrest or perinatal asphyxia.

Aminophosphonic acids have been investigated as neurotransmitter blockers [see M. N. Perkins et al, *Neuroscience Lett.*, 23, 333 (1981); and J. Davies et al, *Neuroscience Lett.*, 21, 77 (1981)]. In particular, compounds such as 2-amino-4-(2-phosphonomethylphenyl)butyric acid and 2-(2-amino-2-carboxy)ethylphenylphosphonic acid have been synthesized for evaluation as antagonists in blocking the action of the neurotransmitter compounds L-glutamic acid and L-aspartic acid [K. Matoba et al, "Structural Modification of Bioactive Compounds II. Syntheses of Aminophosphonic Acids", *Chem. Pharm. Bull.*, 32, (10) 3918-3925 (1984)].

U.S Pat. No. 4,657,899 to Rzeszotarski et al describes a class of ω-[2-(phosphonoalkylenyl)phenyl]-2-aminoalkanoic acids characterized as being selective excitatory amino acid neurotransmitter receptor blockers. These compounds are mentioned for use as anticonvulsants, antiepileptics, analgesics and cognition enhancers. Typical compounds of the class include 3-[2-phosphonomethylphenyl]-2-aminopropanoic acid and 3-[2-(2-phosphonoethyl)phenyl]-2-aminopropanoic acid. European Patent Application 203,891 of Hutchison et al. describes phosphonoalkyl substituted pipecolic acid derivatives useful for treatment of nervous system disorders in mammals and as antagonists of the NMDA sensitive excitatory amino acid receptor, an example of which is cis-4-phosphonomethyl-2-piperidine carboxylic acid. West German Patent Application 3,736,016 of Sandoz describes phosphonoalkyl phenylglycines derivatives useful as anticonvulsant and as antagonists of the NMDA receptor, an example of which is 3-(phosphonomethyl)phenylglycine. U.S. application Ser. No. 111,749 filed October 21, 1987 describes certain phosphonoalkylphenylglycine derivatives useful in reducing neurotoxic injury and as anticonvulsants and analgesics, an example of which is 4-(phosphonomethyl)phenylglycine.

Other classes of compounds have been tested as agonists in blocking NMDA- or KA-induced neurotoxicity [J. W. Olney et al., "The Anti-Excitotoxic Effects of Certain Anesthetics, Analgesics and Sedative-Hypnotics", *Neuroscience Letters*, 68, 29-34 (1986)]. The tested compounds included phencylidine, ketamine, cyclazocine, kynurenate and various barbiturates such as secobarbital, amobarbital and pentobarbital.

DESCRIPTION OF THE INVENTION

Control of neuropathological processes and the neurodegenerative consequences thereof in mammals is provided by treating a mammal susceptible to neurologic injury with a compound of a class characterized in having activity as antagonists at a major neuronal excitatory amino acid receptor site. This class of NMDA antagonist compounds is also expected to contain compounds having anti-convulsant and analgesic activity. Such NMDA antagonist compounds may be selected from a class of phosphono-hydroisoquinoline compounds defined by Formula I:

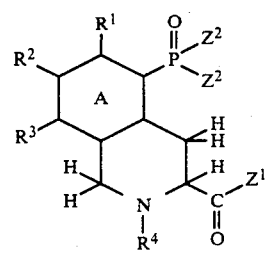

wherein each of $R^1$ through $R^3$ is independently selected from hydrido, alkyl, haloalkyl, halo, cyano, nitro and groups represented by $-OR^5$, $-SR^5$,

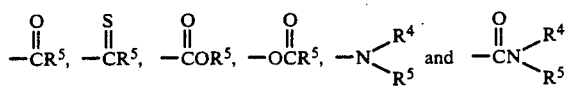

wherein $R^5$ is selected from hydrido, alkyl, aryl and aralkyl; and wherein $R^4$ is selected from hydrido, alkyl, acyl, aralkyl and

and wherein each of $Z^1$ and $Z^2$ is independently selected from $-OR^5$, $SR^5$,

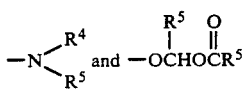

wherein $R^5$ is defined as before; and wherein the A ring can be either saturated, partially unsaturated or fully unsaturated, i.e., an aromatic ring. Within this class of phosphono-hydroisoquinolines of the invention are the pharmaceutically acceptable salts of the compounds of Formula I, including acid addition salts, base addition salts including alkali metal salts. Also included within this class of compounds of the invention are tautomeric forms of the defined compounds and isomeric forms including diastereomers and enantiomers.

A preferred class of compounds within Formula I consists of those compounds wherein each of $R^1$ to $R^5$ is independently selected from hydrido, alkyl, haloalkyl, halo, cyano, nitro, $-OR^5$ and $-SR^5$; wherein $R^5$ is selected from hydrido, alkyl, aryl and aralkyl; and wherein $R^4$ is selected from hydrido, alkyl, acyl, aralkyl and $-COOR^5$; wherein each of $Z^1$ and $Z^2$ is independently selected from $-OR^5$, $-SR^5$, $NR^4R^5$ and $-OCHR^5OCOR^5$; and wherein the A ring can be either saturated, partially unsaturated or fully unsaturated (aromatic).

A more preferred class of compounds within Formula I consists of those compounds wherein each of $R^1$ to $R^5$ is independently selected from hydrido, alkyl, haloalkyl, halo, cyano, $-OR^5$; wherein $R^5$ is selected from hydrido and alkyl; wherein $R^4$ is selected from hydrido, alkyl, acyl, aralkyl and $-COOR^5$; wherein each of $Z^1$ and $Z^2$ is independently selected from $-OR^5$, $NR^4R^5$ and $-OCHR^5OCOR^5$; and wherein the A ring can be either saturated, partially unsaturated or fully unsaturated (aromatic).

An even more preferred class of compounds within Formula I consists of those compounds wherein each of $R^1$, $R^2$ and $R^3$ is hydrido; wherein $R^4$ is selected from hydrido, alkyl, acyl, aralkyl and $-COOR^5$; wherein $R^5$ is selected from hydrido and alkyl; wherein each of $Z^1$ and $Z^2$ is independently selected from $-OR^5$, $NR^4R^5$ and $-OCHR^5OCOR^5$; and wherein the A ring can be either saturated, partially unsaturated or fully unsaturated (aromatic).

A more highly preferred class of compounds within Formula I consists of those compounds wherein each of $R^1$, $R^2$ and $R^3$ is hydrido; wherein $R^4$ is selected from hydrido, acyl and $-COOR^5$; wherein $R^5$ is selected from hydrido and alkyl; wherein $Z^1$ is selected from $-OR^5$, $NR^4R^5$ and $-OCHR^5OCOR^5$; wherein $Z^2$ is hydroxyl; and wherein the A ring can be either saturated, partially unsaturated or fully unsaturated (aromatic).

A still more highly preferred class of compounds within Formula I consists of those compounds wherein each of $R^1$, $R^2$, $R^3$, $R^4$ and $R^5$ is hydrido; wherein each of $Z^1$ and $Z^2$ is OH, and wherein the A ring can be either saturated, partially unsaturated or fully unsaturated (aromatic).

A most highly preferred class of compounds within Formula I consists of those compounds wherein each of $R^1$, $R^2$, $R^3$, $R^4$ and $R^5$ is hydrido; wherein each of $Z^1$ and $Z^2$ is hydroxyl and wherein the A ring is fully unsaturated (aromatic).

An example of a specific, most highly preferred compound within Formula I is 5-phosphono-3-carboxy-1,2,3,4-tetrahydroisoquinoline. This compound exists as a racemic mixture, as the dextro-isomer and as the levo-isomer. Also, this compound may be in the form of a salt, including alkali metal salts such as the sodium salt.

The term "hydrido" denotes a single hydrogen atom (H) which may be attached, for example, to a carbon atom or to an oxygen atom to form an hydroxyl group. Where the term "alkyl" is used, either alone or within other terms such as "haloalkyl", "aralkyl" and "hydroxyalkyl", the term "alkyl" embraces linear or branched radicals having one to about ten carbon atoms. Preferred alkyl radicals are "lower alkyl" radicals having one to about five carbon atoms. The term "haloalkyl" embraces radicals wherein any one or more of the carbon atoms is substituted with one or more halo groups, preferably selected from bromo, chloro and fluoro. Specifically embraced by the term "haloalkyl" are monohaloalkyl, dihaloalkyl and polyhaloalkyl groups. A monohaloalkyl group, for example, may have either a bromo, a chloro, or a fluoro atom within the group. Dihaloalkyl and polyhaloalkyl groups may be substituted with two or more of the same halo groups, or may have a combination of different halo groups. A dihaloalkyl group, for example, may have two bromo atoms, such as a dibromomethyl group, or two chloro atoms, such as a dichloromethyl group, or one bromo atom and one chloro atom, such as bromochloromethyl group. Examples of a polyhaloalkyl are trifluoromethyl, 2,2,2-trifluoroethyl, perfluoroethyl and 2,2,3,3-tetrafluoropropyl groups. The term "alkylthio", as represented by the fragment $-SR^5$, embraces radicals having a linear or branched alkyl portion of one to about ten carbon atoms attached to a divalent sulfur atom, such as a methylthio group. The term "alkoxy", as represented by the fragment $-OR^5$, embraces radicals having a linear or branched alkyl portion of one to about ten carbon atoms attached to an oxygen atom, such as a methoxy group. The term "aryl" embraces aromatic radicals such as phenyl and naphthyl. The term "aralkyl" embraces aryl-substituted alkyl radicals such as benzyl, diphenylmethyl and triphenylmethyl. The terms "benzyl" and "phenylmethyl" are interchangeable.

The term "pharmaceuticaly acceptable salts" embraces forms of a salt of addition with a pharmaceutically utilizable acid, either an inorganic acid such as hydrochloric, hydrobromic, hydroiodic, nitric, carbonic, sulfuric or phosphoric acid, or an appropriate organic acid such as an aliphatic, cycloaliphatic, aromatic, araliphatic, heterocyclic, carboxylic or alkylsulfonic acid, specific examples of which are formic, acetic, propionic, succinic, glycolic, gluconic, lactic, malic, tartaric, citric, ascorbic, glucuronic, maleic, fumaric, pyruvic, aspartic, glutamic, benzoic, anthranilic, p-hydroxybenzoic, salicylic, phenylacetic, mandelic, embonic (pamoic), methanesulfonic, ethanesulfonic, 2-hydroxyethanesulfonic, panthotenic, benzenesulfonic, toluenesulfonic, sulfanilic, mesylic, cyclohexylaminosulfonic, stearic, alginic, β-hydroxybutyric, malonic, galactaric and galacturonic acid. Also embraced are metallic salts made from aluminium, calcium, lithium, magnesium, potassium, sodium and zinc, and organic salts made from benzathine (N,N'-dibenzylethylenediamine), chloroprocaine, choline, diethanolamine, ethylenediamine, meglumine (N-methylglucamine) and procaine.

The compounds of Formula I can possess one or more asymmetric carbon atoms and are thus capable of existing in the form of different, pure optical isomers as well as in the form of racemic or non-racemic mixtures thereof. All these forms fall within the scope of the present invention. The optical isomers can be obtained by resolution of the racemic mixtures according to conventional processes, for example, by formation of diastereomeric salts by treatment with an optically active acid, such as tartaric, diacetyltartaric, dibenzoyltartaric, ditoluoyltartaric and camphorsulfonic acid, followed by separation of the mixture of diastereomers by crystallization and then followed by liberation of the optically active bases from these salts. Separation of optical isomers may also be achieved by passing the isomer mixture through a chiral chromatography column optimally chosen to maximize the separation of the enantiomers of the products of the invention or derivatives thereof. Still another available method involves synthesis of covalent stereoisomeric molecules by reacting the compounds of the invention with an optically pure acid in an activated form or an optically pure isocyanate. The synthesized diastereoisomers can then be separated by conventional means such as chromatography, distillation, crystallization or sublimation and submitted to an hydrolytic step which will deliver the enantiomerically pure compound. The optically active compounds according to Formula I can likewise be obtained by utilizing optically active starting materials. All of these stereoisomers, optical isomers, diastereomers, as well as mixtures thereof, such as racemic mixtures, are within the scope of the invention.

A therapeutically-active compound of Formula I may be administered alone, or in a solvent, but is more likely to be included in a pharmaceutically-acceptable composition. Such pharmaceutical compositions may contain, as active ingredient, at least one compound of Formula I or its salt of addition with a pharmaceutically utilizable acid, and one or more suitable excipients. These compositions are prepared in such a manner that they can be administered by oral, rectal, parental or local route. The compositions can be solids, liquids or gel forms and may be utilized, according to the administration route, in the form of powders, tablets, lozenges, coated tablets, capsules, granulates, syrups, suspensions, emulsion solutions, suppositories or gels. These compositions can likewise comprise another therapeutic agent having an activity similar to or different from that of the compounds of the invention.

Other examples of specific compounds of Formula I are listed in Table I:

Table I

5-Phosphono-3-carboxy-1,2,3,4-tetrahydroisoquinoline hydrochloride;
5-Phosphono-3-carboxy-1,2,3,4-tetrahydroisoquinoline;
6-Methyl-5-phosphono-3-carboxy-1,2,3,4-tetrahydroisoquinoline;
7-Methyl-5-phosphono-3-carboxy-1,2,3,4-tetrahydroisoquinoline;
8-Methyl-5-phosphono-3-carboxy-1,2,3,4-tetrahydroisoquinoline;
6-Chloro-5-phosphono-3-carboxy-1,2,3,4-tetrahydroisoquinoline;
7-Chloro-5-phosphono-3-carboxy-1,2,3,4-tetrahydroisoquinoline;
8-Chloro-5-phosphono-3-carboxy-1,2,3,4-tetrahydroisoquinoline;
(D)-5-Phosphono-3.carboxy-1,2,3,4-tetrahydroisoquinoline;
(L)-5-Phosphono-3-carboxy-1,2,3,4-tetrahydroisoquinoline;
5-Phosphono-3-(ethoxycarbonyl)-1,2,3,4-tetrahydroisoquinoline;
5-(Ethyl phosphono).3-carboxy-1,2,3,4-tetrahydroisoquinoline;
3-cis-carboxy-5-cis-phosphono-cis-2-azadecalin;
3-cis-carboxy-5-trans-phosphono-cis-2-azadecalin;
3-trans-carboxy-5-trans-phosphono-cis-2-azadecalin;
3-trans-carboxy-5-cis-phosphono-cis-2-azadecalin;
3-cis-carboxy-5-cis-phosphono-trans-2.azadecalin;
3-cis-carboxy-5-trans-phosphono-trans-2-azadecalin;
3-trans-carboxy-5.trans-phosphono-trans-2-azadecalin; and
3-trans-carboxy-5-cis-phosphono-trans-2-azadecalin.

Compounds of Formula I may be prepared in accordance with the following general procedure:

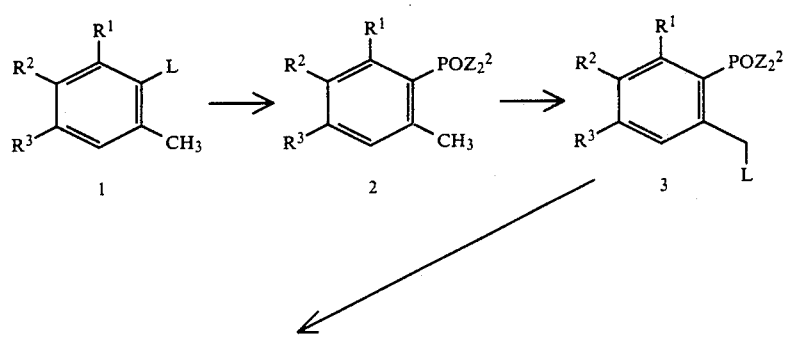

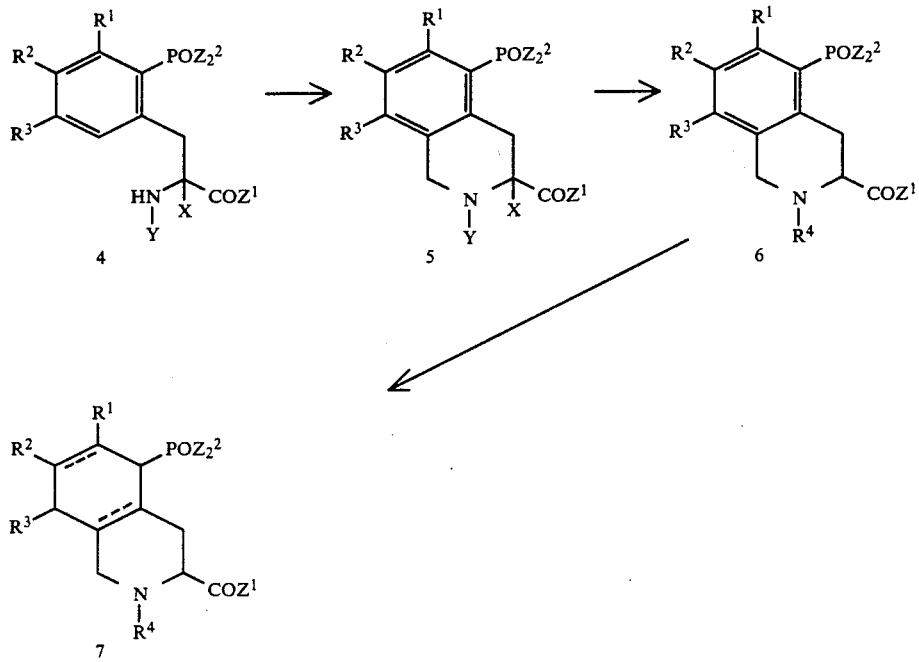

One process which can be used to synthesize the products of the invention starts with an ortho toluene derivative of Compound 1 where each of $R^1$, $R^2$ and $R^3$ has the values defined previously and L is a good leaving group such as, for example, halogen, mesylate, tosylate, brosylate and acetate. These ortho toluene derivatives may be treated with dialkylphosphites in the presence of a palladium catalyst or treated first with magnesium in an aprotic anhydrous solvent to form the Grignard reagent which is then reacted further with a chloro dialkylphosphate reagent. The reaction is best achieved by mixing appropriate quantities of the reagents either neat or in a solvent like toluene, tetrahydrofuran, ether or in a protic solvent in the case of the palladium catalyzed reaction, according to the solubility of the reagents, and the reaction temperature can vary from about 0° C. to reflux of the reaction mixture. In the second step of the process, the methyl group of Compound 2 is oxidized to Compound 3. This step is best achived by treating Compound 2 with an agent able to deliver halogen atoms such as N-bromosuccinimide or N-chlorosuccinimide. The reaction is best conducted in an halogenated solvent such as chloroform, dichloromethane, tetrachloromethane or trichloroethylene at a temperature between 0° C. and reflux temperature of the solvent, with or without irradiation, and in the presence or not of a radical initiator such as azobisisobutyronitrile (AIBN). The leaving group is substituted in the third step with a glycine synthon such as diethylmalonate, acetamidomalonate (X=COOR$^5$, Y=CH$_3$CO), formamidomalonate (X=COOR$^5$, Y=HCO), trifluoroacetamidomalonate (X=COOR$^5$, Y=CF$_3$CO), methylsulfonamidomalonate (X=COOR$^5$, Y=CH$_3$SO$_2$), N-(diphenylmethylene)glycine ethyl ester (X=H, Y=$\phi_2$C=) or ethyl isocyanoacetate (X=H, Y=:C=). Compound 4 obtained from this reaction may require some transformation of the nitrogen substituent Y. For instance, the formamido, acetamido, isocyano and diphenylmethylene residues can be hydrolyzed to the free amine which will be either acylated or sulfonated to provide a compound more suitable for the experimental conditions of the next step. If diethylmalonate has been used as the glycine synthon, it may be necessary to conduct a mono hydrolysis of the diester by stirring the compound in the presence of one equivalent of an alkali hydroxide such as lithium, sodium or potassium hydroxide at room temperature. The acid is carefully transformed into the azido acid either by the mixed anhydride method or by the use of a specific reagent such as diphenylphosphoryl azide. The azido acid is transformed into the amine by thermolysis in an aprotic solvent such as toluene and quenching of the isocyanate formed with dilute HCl.

The cyclization is best conducted by stirring Compound 4 in the presence of paraformaldehyde or trioxane and methanesulfonic acid in 1,2-dichloroethane or in an other chlorinated solvent. When R$^4$ is equal to acyl or alkoxycarbonyl, complete hydrolysis of Z$^1$, Z$^2$ and R$^4$ can be acheived by an aqueous acid solution, such as 6 N HCl or other mineral acid solution. Selective hydrolysis of R$^4$ can be achieved in an acidic alcoholic solution. Selective cleavage of Z$^1$ and Z$^2$ can be achieved by catalytic hydrogenation when Z$^1$ or Z$^2$ is benzyloxy. Various selective deprotection schemes are possible depending on the nature of R$^4$, Z$^1$ and Z$^2$. When R$^1$, R$^2$ or R$^3$ is hydrolyzable the preferred method of deprotection is by catalytic hydrogenation of hydrogenolytically labile groups.

The perhydroisoquinolines can be prepared by the catalytic hydrogenation of the fully or partially deprotected tetrahydroisoquinolines 5 using various metal catalysts such as Pd, Pt, Ni, Ru and Rh. Partially hydrogenated material can be prepared by selective reduction methods, such as the Birch reduction, to obtain dienes followed by selective catalytic hydrogenation to obtain the mono-unsaturated products or the fully saturated compound. The advantage in using different methods of reduction is that different isomers could be obtained among the different racemic mixtures theoretically available.

The following Examples are detailed descriptions of the methods of preparation of compounds of Formula I. These detailed preparations fall within the scope of, and serve to exemplify, the above described general procedures which form part of the invention. These Examples are presented for illustrative purposes only and are not intended as a restriction on the scope of the invention. All parts are by weight unless otherwise indicated. Most of the commercially-available starting materials were obtained from Aldrich Chemical Co., Milwaukee, Wis.

EXAMPLE I

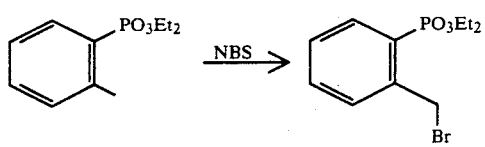

Diethyl 2-methylphenylphosphonate (6.84 gm) and N-bromosuccinimide (NBS) (5.87 gm) were combined in CCl$_4$ (60 mL). A small amount of azo-bisisobutyronitrile was added and the mixture was heated to reflux. After 6 hours, the NBS had been completely consumed and the orange colored reaction mixture had become a pale yellow. The reaction mixture was cooled to room temperature and the insoluble succinimide removed by filtration. Removal of the solvent on a rotary evaporator afforded a yellow oil. The oil was chromatographed on silica gel (125 gm) eluting with ethyl acetate. The appropriate fractions were pooled and concentrated to afford the product as a colorless oil.

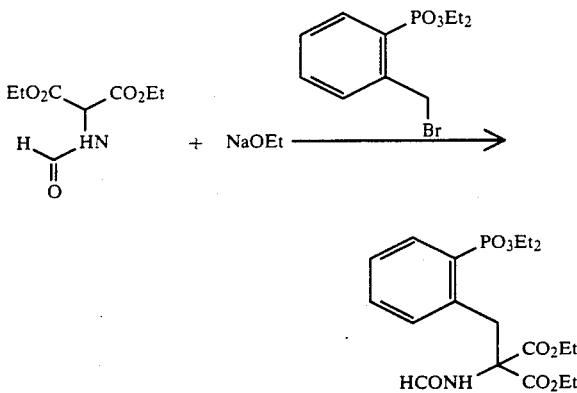

Sodium (82 mg) was dissolved in anhydrous ethanol (6 ml) under a nitrogen atmosphere. Diethyl formamidomalonate (725 mg) was then added with stirring. The reaction mixture became homogeneous and then a precipitate began to form. The reaction mixture was briefly heated to reflux and then allowed to cool. The 2-(diethylphosphono)benzyl bromide (1 gm) was then added and the reaction allowed to stir at room temperature for 20 hours. The reaction mixture was partitioned between H$_2$O (30 ml) and Et$_2$O (30 ml). The lower aqueous layer was extracted with fresh Et$_2$O (30 ml) and the combined Et$_2$O layers washed once with saturated NaCl (30 ml). The Et$_2$O layer was then dried (MgSO$_4$) and concentrated to an oil. The oil was chromatographed on silica gel using ethyl acetate as the eluting solvent. The appropriate fractions were pooled and concentrated to afford the product as a clear oil.

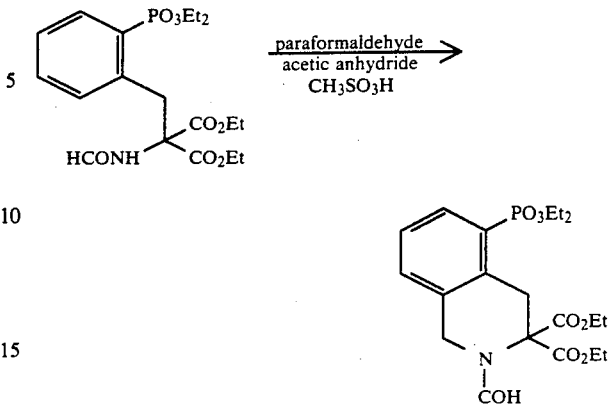

Diethyl 2-(2-(diethylphosphono)benzyl)formamidomalonate (430 mg) was combined with paraformaldehyde (31 mg) and acetic anhydride (94 µl) in 1,2-dichloroethane (3.6 ml) containing methanesulfonic acid (0.4 ml) and allowed to stir at room temperature for 7 days. The reaction mixture was diluted with Et$_2$O (25 ml) and extracted with H$_2$O (10 ml). The H$_2$O layer was extracted with Et$_2$O (25 ml) and the combined Et$_2$O layers dried (MgSO$_4$) and concentrated to an oil. The oil was chromatographed on silica gel (50 gm) equilibrated with CH$_2$Cl$_2$. The column was eluted with CH$_2$Cl$_2$ (100 ml), 1% EtOH/CH$_2$Cl$_2$ (200 ml), and then the eluent was held at 2% EtOH/CH$_2$Cl$_2$. Fractions of about 10 ml were collected. A few minor impurities eluted followed by the product in fractions 71–79 and unreacted starting material in fractions 82–92. The appropriate fractions were pooled and concentrated to an oil.

EXAMPLE II

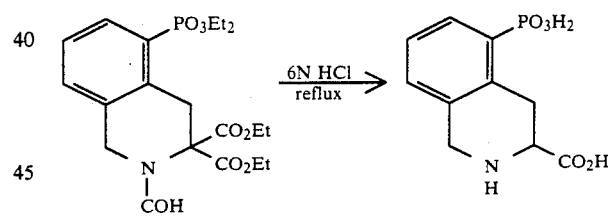

N-Formyl-3-bis(ethoxycarbonyl)-5-(diethylphosphono)-1,2,3,4-tetrahydroisoquinoline (100 mg) was combined with 6 N HCl (20 ml) and heated to reflux for 18 hours. The solvent was removed on a rotary evaporator and the resulting white solid dissolved in H$_2$O (20 ml) and reconcentrated. This process was repeated with ethanol and the final product dried in vacuo.

| | Elemental Analysis: | |
|---|---|---|
| | Theory + H$_2$O | Found |
| C | 38.54 | 38.10 |
| H | 4.85 | 4.90 |
| N | 4.49 | 4.34 |

$^1$H NMR (D$_2$O) δ* 3.38 (m,1 H), 3.78 (m,1 H), 4.40 (t,1 H), 4.44 (m,2 H), 7.36 (m,2 H), 7.75 (m,1 H).
* relative to HOD peak at 4.72 ppm.

BIOLOGICAL EVALUATION

Binding Assays:

[Pullan, L. M., Olney, J. W., Price, M. T., Compton, R. P., Hood, W. F., Michel J., Monahan J. B., "Excitatory Amino Acid Receptor Potency and Subclass Specificity of Sulfur-Containing Amino Acids", *Journal of Neurochemistry*, 49 1301-1307, (1987)].

Synaptic plasma membranes (SPM) were prepared as previously described [Monahan, J. B. and Michel, J., "Identification and Characterization of an N-methyl-D-aspartate-specific L[$^3$H]glutamate Recognition Site in Synaptic Plasma Membranes, *J. Neurochem.*, 48, 1699-1708 (1987)]. The SPM were stored at a concentration of 10-15 mg/ml in 0.32 M sucrose, 0.5 mM EDTA, 1 mM MgSO$_4$, 5 mM Tris/SO$_4$, pH 7.4, under liquid nitrogen. The identity and purity of the subcellular fractions were confirmed by both electron microscopy and marker enzymes. Protein concentrations were determined by using a modification of the method of Lowry [Ohnishi, S. T. and Barr, J. K., "A Simplified Method of Quantitating Proteins Using the Biuret and Phenol Reagents", *Anal. Biochem.*, 86, 193-197 (1978)].

The SPM were treated identically for the [$^3$H]AMPA (QUIS), [$^3$H]kainate and sodium-dependent L-[$^3$H]-glumatate binding assays. The SPM were thawed at room temperature, diluted twenty-fold with 50mM Tris/acetate, pH 7.4, incubated at 37° C. for 30 minutes, and centrifuged at 100,000 g for 15 minutes. The dilution, incubation and centrifugation were repeated a total of three times.

Prior to use in the NMDA-specific L-[$^3$H]-glutamate binding assay, the SPM were thawed, diluted twenty fold with 50 mM Tris/acetate (pH 7.4 containing 0.04% (v/v) Triton X-100), incubated for 30 minutes at 37° C. and centrifuged as described above. The Triton X-100 treated membranes were washed with 50 mM Tris/acetate (pH 7.4) and centrifuged at 100,000 g for 15 minutes a total of four times.

The basic procedure for the receptor subclass binding assays was similar. This general method involved adding the radioligand (12.5 nM L-[$^3$H] glutamate; 0.5 nM [$^3$H]kainate or 10 nM [$^3$H]AMPA) to the appropriate concentration of the test compound and initiating the assay by the addition of ice cold synaptic plasma membranes (0.2-0.45 mg). The binding assays were performed in 1.5 mL centrifuge tubes with the total volume adjusted to 1.0 mL. Additions of test compounds were made in 50 mM Tris/acetate (pH 7.4) and incubations were carried out at 0°-4° C. The incubation time for each of the NMDA and the AMPA binding assays was 10 minutes, for the kainate binding assay 60 minutes and for the sodium-dependent glutamate binding assay 15 minutes. The AMPA binding assay contained 100 mM KSCN and the sodium-dependent glutamate binding assay contained 150 mM sodium acetate in addition to the previously described reagents.

To terminate the incubation, the samples were centrifuged for 15 minutes at 12,000 g and 4° C. in a Beckman Microfuge 12. The supernatant was aspirated and the pelleted membranes dissolved in Beckman BTS-450 tissue solubilizer for a minimum of 6 hours at room temperature. Beckman MP scintillation cocktail containing 7 mL/1 acetic acid was then added and the samples counted on a Beckman LS 5800 or 3801 liquid scintillation counter with automatic corrections for quenching and counting efficiency.

Nonspecific binding was defined as the residual binding in the presence of either excess L-glutamate (0.1-0.4 mM), kainate (0.01 mM), or NMDA (0.5 mM), and was 15-25% of the total binding in the NMDA binding assay, 19-27% in the AMPA binding assay, 20-30% in the kainate binding assay and 10-15% in the sodium-dependent binding assay. Radioligand binding to the synaptic plasma membranes was analyzed using Scatchard and Hill transformations and the $K_i$ values of the compounds determined using logit-log transformations. Calculations and regression analysis were performed using templates developed for Lotus 1, 2, 3 as previously described [Pullan, L. M. "Automated Radioligand Receptor Binding Analysis with Templates for Lotus", *Computer Appln. Biosci.*, 3 131 (1987)]. Binding results are reported in Table II for example compounds of the invention. Included in Table II are binding data for D,L-AP7[D,L-2-amino-7-phosphonoheptanoic acid].

TABLE II

| | RECEPTOR BINDING DATA | | |
| | Binding ($\mu$M) | | |
| Compound | NMDA | KA | Quis |
|---|---|---|---|
| D,L-AP7 | 5.4 | >300 | >300 |
| D-AP7 | 4.0 | >300 | >300 |
| Ex. II | 1.6 | ~300 | >300 |

TCP Modulation Assay

The effect on the TCP (1-[1-(2-thienyl)cyclohexyl]-piperidine) binding was measured in rat brain synaptic membranes (SPM) prepared as previously described [J. B. Monahan & J. Michel; J. Neurochem. 48:1699-1708 (1987)]. Prior to their use in the binding assay, frozen SPM were thawed, diluted twenty fold with 50 mM Tris/acetate (pH 7.4 containing 0.04% (v/v) Triton X-100), incubated for 30 min. at 37° C. and centrifuged at 95,000xg for 15 min. The Triton X-100 treated SPM were washed with 5 mM Tris/HCl, pH 7.4 and centrifuged a total of six times. The compound of Example II was incubated at different concentrations with SPM (0.2-0.4 mg protein) and 2 nM tritiated TCP, in a total volume of 0.5 ml of 5 mM Tris/HCl buffer pH 7.4 at 25° C. for 60 min. The samples were filtered through glass fiber filters (Schleicher & Schuell #32) which have been pretreated with 0.05% (v/v) polyethylenimine, washed 4 times with 2 ml of ice-cold 5 mM Tris/HCl buffer, and then counted on a Beckman LS 5800 liquid scintillation counter with automatic corrections for quenching and counting efficiency. Inhibition of TCP binding was measured as a decrease in the binding in the presence of 0.05 mM L-glutamate. Non-specific binding was defined as the residual binding in the presence of 60 mM phencyclidine.

Result: The compound of Example II inhibits 64% of TCP binding at 5 $\mu$M and 91% at 50 $\mu$M.

Administration of compounds within Formula I to humans can be by any technique capable of introducing the compounds into the bloodstream of a human patient, including oral administration, and by intravenous, intramuscular and subcutaneous injections.

Compounds indicated for prophylactic therapy will preferably be administered in a daily dose generally in a range from about 0.1 mg to about 100 mg per kilogram of body weight per day. A more preferred dosage will be a range from about 1 mg to about 100 mg per kilogram of body weight. Most preferred is a dosage in a range from about 1 to about 50 mg per kilogram of body weight per day. A suitable dose can be administered, in multiple sub-doses per day. These sub-doses may be administered in unit dosage forms. Typically, a dose or sub-dose may contain from about 1 mg to about 100 mg of active compound per unit dosage form. A more preferred dosage will contain from about 2 mg to about 50 mg of active compound per unit dosage form. Most preferred is a dosage form containing from about 3 mg to about 25 mg of active compound per unit dose.

The active compound is usually administered in a pharmaceutically-acceptable formulation, although in some acute-care situations a compound of Formula I may be administered alone. Such formulations may comprise the active compound together with one or more pharmaceutically-acceptable carriers or diluents. Other therapeutic agents may also be present in the formulation. A pharmaceutically-acceptable carrier or diluent provides an appropriate vehicle for delivery of the active compound without introducing undesirable side effects. Delivery of the active compound in such formulations may be by various routes including oral, nasal, topical, buccal and sublingual, or by parenteral administration such as subcutaneous, intramuscular, intravenous and intradermal routes.

Formulations for oral administration may be in the form of capsules containing the active compound dispersed in a binder such as gelatin or hydroxypropylmethyl cellulose, together with one or more of a lubricant, preservative, surface-active or dispersing agent. Such capsules or tablets may contain controlled-release formulation as may be provided in a dispersion of active compound in hydroxypropylmethyl cellulose.

Formulations for parenteral administration may be in the form of aqueous or non-aqueous isotonic sterile injection solutions or suspensions. These solutions and suspensions may be prepared from sterile powders or granules having one or more of the carriers or diluents mentioned for use in the formulations for oral administration.

Although this invention has been described with respect to specific embodiments, the details of these embodiments are not to be construed as limitations. Various equivalents, changes and modifications may be made without departing from the spirit and scope of this invention, and it is understood that such equivalent embodiments are part of this invention.

What is claimed is:

1. A compound of the formula

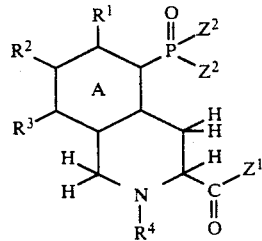

wherein each of $R^1$ through $R^3$ is independently selected from hydridro, linear alkyl and linear haloalkyl each having one to about ten carbon atoms, halo, and groups represented by $-OR^5$, $-SR^5$,

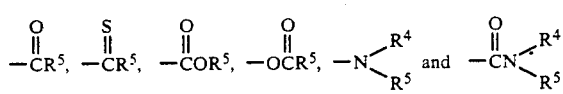

wherein $R^5$ is selected from hydrido, alkyl, phenyl, naphthyl, benzyl, diphenylmethyl and triphenylmethyl; and wherein $R^4$ is selected from hydrido, alkyl, acyl of one to about ten carbon atoms, benzyl, diphenylmethyl and triphenylmethyl; and

and wherein each of $Z^1$ and $Z^2$ is independently selected from $-OR^5$ and $SR^5$, wherein $R^5$ is defined as before; and wherein the A ring is an aromatic ring; or a pharmaceutically-acceptable salt thereof.

2. Compound of claim 1 wherein each of $R^1$, $R^2$ and $R^3$ is independently selected from hydrido, linear alkyl and linear haloalkyl each having one to about ten carbon atoms, halo, $-OR^5$ and $-SR^5$; wherein $R^5$ is selected from hydrido and alkyl.

3. Compound of claim 2 wherein each of $R^1$ to $R^3$ is independently selected from hydrido, linear alkyl and linear haloalkyl each having one to about ten carbon atoms, halo and $-OR^5$, wherein $R^5$ is selected from hydrido and alkyl; wherein each of $Z^1$ and $Z^2$ is $-OR^5$; wherein $R^5$ is selected from hydrido and alkyl.

4. Compound of claim 3 wherein each of $R^1$, $R^2$ and $R^3$ is hydrido.

5. Compound of claim 4 wherein $R^4$ is selected from hydrido, acyl of one to about ten carbon atoms, and $-COOR^5$; wherein $R^5$ is selected from hydrido and alkyl; and wherein $Z^2$ is hydroxyl.

6. Compound of claim 3 wherein each of $R^1$ to $R^5$ is hydrido; and wherein each of $Z^1$ and $Z^2$ is hydroxyl.

7. Compound of claim 1 selected from the group consisting of compounds and pharmaceutically-acceptable salts thereof, as follows:

3-carboxy-5-phosphono-1,2,3,4-tetrahydroisoquinoline hydrochloride;

3-carboxy-5-phosphono-3-carboxy-1,2,3,4-tetrahydroisoquinoline;

3-carboxy-6-methyl-5-phosphono-1,2,3,4-tetrahydroisoquinoline;

3-carboxy-7-methyl-5-phosphono-1,2,3,4-tetrahydroisoquinoline;

3-carboxy-8-methyl-5-phosphono-1,2,3,4-tetrahydroisoquinoline;

3-carboxy-6-chloro-5-phosphono-1,2,3,4-tetrahydroisoquinoline;

3-carboxy-7-chloro-5-phosphono-1,2,3,4-tetrahydroisoquinoline;

3-carboxy-8-chloro-5-phosphono-1,2,3,4-tetrahydroisoquinoline;

(D)-3-carboxy-5-phosphono-1,2,3,4-tetrahydroisoquinoline;

(L)-3-carboxy-5-phosphono-1,2,3,4-tetrahydroisoquinoline;

3-(ethoxycarbonyl)-5-phosphono-1,2,3,4-tetrahydroisoquinoline; and 3-carboxy-5-(ethylphosphono)-1,2,3,4-tetrahydroisoquinoline.

8. Compound of claim 6 which is D,L-3-carboxy-5-phosphono-1,2,3,4-tetrahydroisoquinoline; or a pharmaceutically-acceptable salt thereof.

9. Compound of claim 6 which is D-3-carboxy-5-phosphono-1,2,3,4-tetrahydroisoquinoline; or a pharmaceutically-acceptable salt thereof.

10. A pharmaceutical composition comprising a therapeutically-effective amount of a compound and a pharmaceutically-acceptable carrier or diluent, said compound selected from a family of compounds of the formula

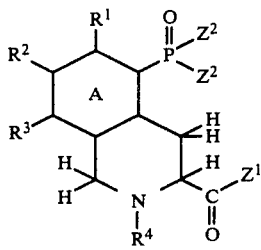

wherein each of $R^1$ through $R^3$ is independently selected from hydrido, linear alkyl and linear haloalkyl each having one to about ten carbon atoms, halo, and groups represented by $-OR^5$, $-SR^5$,

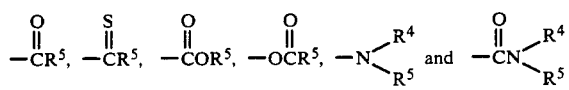

wherein $R^5$ is selected from hydrido, alkyl, phenyl, naphthyl, benzyl, diphenylmethyl and triphenylmethyl; and wherein $R^4$ is selected from hydrido, alkyl, acyl of one to about ten carbon atoms, benzyl, diphenylmethyl and triphenylmethyl; and

and wherein each of $Z^1$ and $Z^2$ is independently selected from $-OR^5$ and $SR^5$, wherein $R^5$ is defined as before; and wherein the A ring is an aromatic ring; or a pharmaceutically-acceptable salt thereof.

11. The composition of claim 10 wherein each of $R^1$, $R^2$ and $R^3$ is independently selected from hydrido, linear alkyl and linear haloalkyl each having one to about ten carbon atoms, halo, $-OR^5$ and $-SR^5$; wherein $R^5$ is selected from hydrido and alkyl.

12. The composition of claim 14 wherein each of $R^1$ to $R^3$ is independently selected from hydrido, linear alkyl and linear haloalkyl each having one to about ten carbon atoms, halo and $-OR^5$, wherein $R^5$ is selected from hydrido and alkyl; wherein each of $Z^1$ and $Z^2$ is $-OR^5$; wherein $R^5$ is selected from hydrido and alkyl.

13. The composition of claim 12 wherein each of $R^1$, $R^2$ and $R^3$ is hydrido.

14. The composition of claim 13 wherein $R^4$ is selected from hydrido, acyl of one to about ten carbon atoms, and $-COOR^5$; wherein $R^5$ is selected from hydrido and alkyl; and wherein $Z^2$ is hydroxyl.

15. The composition of claim 13 wherein each of $R^1$ to $R^5$ is hydrido; and wherein each of $Z^1$ and $Z^2$ is hydroxyl.

16. The composition of claim 10 wherein said compound is selected from the group consisting of compounds and pharmaceutically-acceptable salts thereof, as follows:

3-carboxy-5-phosphono-1,2,3,4-tetrahydroisoquinoline hydrochloride;
3-carboxy-5-phosphono-3-carboxy-1,2,3,4-tetrahydroisoquinoline;
3-carboxy-6-methyl-5-phosphono-1,2,3,4-tetrahydroisoquinoline;
3-carboxy-7-methyl-5-phosphono-1,2,3,4-tetrahydroisoquinoline;
3-carboxy-8-methyl-5-phosphono-1,2,3,4-tetrahydroisoquinoline;
3-carboxy-6-chloro-5-phosphono-1,2,3,4-tetrahydroisoquinoline;
3-carboxy-7-chloro-5-phosphono-1,2,3,4-tetrahydroisoquinoline;
3-carboxy-8-chloro-5-phosphono-1,2,3,4-tetrahydroisoquinoline;
(D)-3-carboxy-5-phosphono-1,2,3,4-tetrahydroisoquinoline;
(L)-3-carboxy-5-phosphono-1,2,3,4-tetrahydroisoquinoline;
3-(ethoxycarbonyl)-5-phosphono-1,2,3,4-tetrahydroisoquinoline; and
3-carboxy-5-(ethylphosphono)-1,2,3,4-tetrahydroisoquinoline.

17. The composition of claim 16 wherein said compound is D,L-3-carboxy-5-phosphono-1,2,3,4-tetrahydroisoquinoline; or a pharmaceutically-acceptable salt thereof.

18. The composition of claim 16 wherein said compound is D-3-carboxy-5-phosphono-1,2,3,4-tetrahydroisoquinoline; or a pharmaceutically-acceptable salt thereof.

19. A method to produce analgesia, or to treat a subject susceptible to or inflicted with neurotoxic injury, or ischemia or convulsions, which method comprises administering to the subject an effective amount of an NMDA antagonist compound of the formula

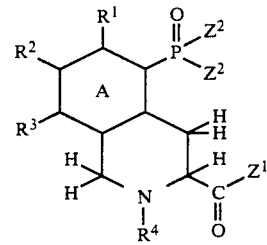

wherein each of $R^1$ through $R^3$ is independently selected from hydrido, linear alkyl and linear haloalkyl each having one to about ten carbon atoms, halo, and groups represented by $-OR^5$, $-SR^5$,

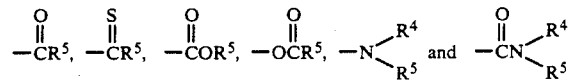

wherein $R^5$ is selected from hydrido, alkyl, phenyl, naphthyl, benzyl, diphenylmethyl and triphenylmethyl; and wherein $R^4$ is selected from hydrido, alkyl, acyl of one to about ten carbon atoms, benzyl, diphenylmethyl and triphenylmethyl; and

and wherein each of $Z^1$ and $Z^2$ is independently selected from $-OR^5$ and $SR^5$, wherein $R^5$ is defined as before; and wherein the A ring is an aromatic ring; or a pharmaceutically-acceptable salt thereof.

20. The method of claim 19 wherein each of $R^1$, $R^2$ and $R^3$ is independently selected from hydrido, linear alkyl and linear haloalkyl each having one to about ten carbon atoms, halo, —OR$^5$ and —SR$^5$; wherein R$^5$ is selected from hydrido and alkyl.

21. The method of claim 20 wherein each of R$^1$ to R$^3$ is independently selected from hydrido, linear alkyl and linear haloalkyl each having one to about ten carbon atoms, halo and —OR$^5$, wherein R$^5$ is selected from hydrido and alkyl; wherein each of Z$^1$ and Z$^2$ is —OR$^5$; wherein R$^5$ is selected from hydrido and alkyl.

22. The method of claim 21 wherein each of R$^1$, R$^2$ and R$^3$ is hydrido.

23. The method of claim 22 wherein R$^4$ is selected from hydrido, acyl of one to about ten carbon atoms, and —COOR$^5$; wherein R$^5$ is selected from hydrido and alkyl; and wherein Z$^2$ is hydroxyl.

24. The method of claim 23 wherein each of R$^1$ to R$^5$ is hydrido; wherein each of Z$^1$ and Z$^2$ is hydroxyl.

25. The method of claim 19 wherein said compound is selected from the group consisting of compounds and pharmaceutically-acceptable salts thereof, as follows:
3-carboxy-5-phosphono-1,2,3,4-tetrahydroisoquinoline hydrochloride;
3-carboxy-5-phosphono-3-carboxy-1,2,3,4-tetrahydroisoquinoline;
3-carboxy-6-methyl-5-phosphono-1,2,3,4-tetrahydroisoquinoline;
3-carboxy-7-methyl-5-phosphono-1,2,3,4-tetrahydroisoquinoline;
3-carboxy-8-methyl-5-phosphono-1,2,3,4-tetrahydroisoquinoline;
3-carboxy-6-chloro-5-phosphono-1,2,3,4-tetrahydroisoquinoline;
3-carboxy-7-chloro-5-phosphono-1,2,3,4-tetrahydroisoquinoline;
3-carboxy-8-chloro-5-phosphono-1,2,3,4-tetrahydroisoquinoline;
(D)-3-carboxy-5-phosphono-1,2,3,4-tetrahydroisoquinoline;
(L)-3-carboxy-5-phosphono-1,2,3,4-tetrahydroisoquinoline;
3-(ethoxycarbonyl)-5-phosphono-1,2,3,4-tetrahydroisoquinoline; and
3-carboxy-5-(ethylphosphono)-1,2,3,4-tetrahydroisoquinoline.

26. The method of claim 25 wherein said compound is D,L-3-carboxy-5-phosphono-1,2,3,4-tetrahydroisoquinoline; or a pharmaceutically-acceptable salt thereof.

27. The method of claim 25 wherein said compound is D-3-carboxy-5-phosphono-1,2,3,4-tetrahydroisoquinoline; or a pharmaceutically-acceptable salt thereof.

* * * * *